(12) United States Patent
Jacovella et al.

(10) Patent No.: US 10,874,682 B2
(45) Date of Patent: Dec. 29, 2020

(54) COMPOSITIONS AND THE USE THEREOF FOR TREATING OR PREVENTING ROSACEA

(71) Applicant: NESTLÉ SKIN HEALTH SA, Lausanne (CH)

(72) Inventors: Jean Jacovella, Antibes (FR); Olivier Roye, Fayence (FR); André Jomard, Saint Vallier de Thiey (FR)

(73) Assignee: NESTLÉ SKIN HEALTH SA, Lausanne (CH)

( * ) Notice: Subject to any disclaimer, the term of this patent is extended or adjusted under 35 U.S.C. 154(b) by 0 days.

(21) Appl. No.: 16/322,434

(22) PCT Filed: Aug. 4, 2017

(86) PCT No.: PCT/EP2017/069809
§ 371 (c)(1),
(2) Date: Jan. 31, 2019

(87) PCT Pub. No.: WO2018/024888
PCT Pub. Date: Feb. 8, 2018

(65) Prior Publication Data
US 2019/0192545 A1    Jun. 27, 2019

(30) Foreign Application Priority Data

Aug. 4, 2016    (EP) .................... 16306013

(51) Int. Cl.
*A61K 31/7048*    (2006.01)
*A61K 31/196*    (2006.01)
*A61P 17/00*    (2006.01)
*A61P 29/00*    (2006.01)
*A61K 9/00*    (2006.01)

(52) U.S. Cl.
CPC ........ *A61K 31/7048* (2013.01); *A61K 9/0014* (2013.01); *A61K 31/196* (2013.01); *A61P 17/00* (2018.01); *A61P 29/00* (2018.01)

(58) Field of Classification Search
None
See application file for complete search history.

(56) References Cited

U.S. PATENT DOCUMENTS

| | | | |
|---|---|---|---|
| 8,669,233 B2 * | 3/2014 | Jomard | A61K 9/0014 514/30 |
| 9,233,117 B2 * | 1/2016 | Jacovella | A61P 33/14 |
| 9,233,118 B2 * | 1/2016 | Jacovella | A61P 17/00 |
| 2005/0147570 A1 | 7/2005 | Nordsiek et al. | |
| 2014/0256662 A1 | 9/2014 | Kaoukhov et al. | |
| 2016/0120797 A1 * | 5/2016 | Rayudu | A61K 31/7056 424/450 |

FOREIGN PATENT DOCUMENTS

WO    WO 2013/095286 A2    6/2013

OTHER PUBLICATIONS

Goldgar et al., "Treatment Options for Acne Rosacea" American Family Physician vol. 80 No. 5 pp. 461-468 (Year: 2009).*
Steinhoff et al., "Topical Ivermetin 10mg/g and Oral Doxycycline 40 mg Modified-Release: Current Evidence on the Complementary Use of Anti-Inflammatory Rosacea Treatments", Advances in Therapy, Health Communications, Metuchen, NJ, US, vol. 33, No. 9, Jul. 18, 2016, pp. 1481-1501.
"Ivermectin 1% topical cream for papulopustular rosacea", Internet Citation, pp. 1-9, Jul. 2014.
International Search Report issued in PCT/EP2017/069809, dated Aug. 30, 2017.
Written Opinion of the International Searching Authority issued in PCT/EP2017/069809, dated Aug. 30, 2017.

* cited by examiner

*Primary Examiner* — Eric Olson
(74) *Attorney, Agent, or Firm* — Foley & Lardner LLP; Sunit Talapatra

(57) ABSTRACT

The present invention relates to a composition comprising a pharmaceutically acceptable carrier, at least one compound of the avermectin family, and at least one non-steroidal anti-inflammatory compound. The present invention further provides such composition for use in the treatment and/or the prevention of rosacea.

9 Claims, No Drawings

COMPOSITIONS AND THE USE THEREOF FOR TREATING OR PREVENTING ROSACEA

CROSS-REFERENCE TO RELATED APPLICATIONS

This application is the National Phase of International Patent Application No. PCT/EP2017/069809, filed Aug. 4, 2017, published on Feb. 8, 2018 as WO 2018/024888 A1, which claims priority to European Application No. 16306013.0, filed Aug. 4, 2016. The contents of these applications are herein incorporated by reference in their entirety.

The present invention concerns dermatologic field and relates to compositions and the use thereof for the treatment and/or prevention of rosacea.

BACKGROUND OF THE INVENTION

Rosacea is a common chronic and progressive inflammatory dermatosis associated with vasodilatation. Rosacea affects principally central part of the face and is characterized by facial flushes, facial erythema, papules, pustules, telangiectasia and sometimes ocular lesions and rhinophyma. Moreover these primary features are associated with a secondary neurogenic component, more specifically to a cutaneous hyperreactivity of face and neck skin, characterized by the apparition of skin redness, pruritus, feelings of itching, burning, stinging, and rough, flaky skin sensations.

Rosacea is classified into four subtypes according to the degree of primary features, such as vasomotor flushing, persistent erythema, papules and pustules, telangiectasia, phymatous changes and ocular involvement.

Erythematotelangiectatic rosacea (ETR) is mainly characterized by vasomotor flushing and persistent central facial erythema (redness). Telangiectasia (visible blood vessels) are commonly observed but are not essential for the diagnosis of this subtype. Central facial edema, burning or stinging sensations and rough, flaky skin are also symptoms that have sometimes been reported. A history of flushing as the only symptom is commonly found in people with erythematotelangiectatic rosacea. Facial flushing is due to the sudden dilatation of the arterioles of the face (which then takes a red appearance) and may be triggered by emotional stress, hot drink, alcohol, spicy food or temperature changes.

Papulopustular rosacea (PPR) is characterized by persistent central facial erythema and transient inflammatory crops of papules and/or pustules in the center of the face. However, the papules and pustules can also occur in periorificial regions, i.e., around the mouth, nose and eyes. The papulopustular subtype resembles acne vulgaris but comedones (specific to acne) are absent in rosacea. Rosacea and acne may coexist in a same patient, in which case comedones may also be present alongside the papules and pustules suggestive of rosacea. People with papulopustular rosacea sometimes complain of a burning or stinging sensation. Moreover, PPR is also characterized by the presence of inflammatory infiltrates that accompany flares, along with a heightened immune response involving neutrophilic infiltration and increased gene expression of IL8. This subtype is often observed after or at the same time as ETR (including the presence of telangiectasias).

Phymatous rosacea is characterized by a thickening of the skin, irregular surface nodularities and swelling. Patients with this subtype sometimes exhibit prominent, enlarged follicles as well as telangiectasias in the affected areas. The nose is most commonly affected ("rhinophyma") but phymatous rosacea can also involve other areas such as the chin, the forehead, the cheeks and the ears. This subtype essentially affects men and often occurs after or at the same time as ETR or PPR.

Ocular rosacea (or ophthalmic rosacea) exhibits symptoms restricted to the ocular area with blepharitis, conjunctivitis and keratitis. It is characterized by watery or bloodshot eyes (interpalpebral conjunctival hyperemia), foreign body sensation, burning or stinging, dry or itchy eyes, sensitivity to light, blurred vision, conjunctival telangiectasias or eyelid margin telangiectasias or erythema of the eyelid and periocular area. They can occur with or without facial rosacea. The onset may occur before, during or after the onset of skin lesions.

The pathogenesis of rosacea is complex and not yet completely understood. Its etiology is multifactorial. In addition to exogenous factors (including UV light, temperature changes, alcohol, hormonal or emotional factors), it may be due to a higher density of *Demodex folliculorum* mites in rosacea patients. Such factors activate neurovascular and/or immune responses, and consequently inflammatory cascades. Intermittent flares may contribute to the chronicity of rosacea as they are associated with prolonged vasodilation, perivascular inflammation, edema and exposure to cytokines and cellular infiltrates. Moreover, many people who get rosacea have family history of the disease, suggesting a possible role of genetic factors.

Typical treatment of rosacea includes oral or topical administration of antibiotics such as tetracycline, erythromycin, clindamycin, but also metronidazole (an antibacterial agent), low dose of isotretinoin in severe forms or even anti-infectious agents such as azelaic acid.

However, these treatments do not allow to treat efficiently rosacea especially the inflammatory lesions and take several weeks to improve the papulopustular lesions of rosacea. Moreover several side effects have been reported with some of them, such as topical isotretinoin.

The treatment of rosacea with ivermectin, which targets the *Demodex folliculorum* parasite presents on the skin of patients, is also known (U.S. Pat. No. 5,952,372). The treatment of rosacea with a composition comprising diclofenac as active ingredient has already been disclosed in US2011281947.

None of the existing treatments make possible to effectively treat and/or prevent with a very rapid action and few side effects, the symptoms associated with rosacea.

In view of all these various elements, there is a need to produce a more effective treatment for rosacea, which does not have the side effects observed in the prior art. There is in particular a need to produce a composition which confers a greater tolerance of the active ingredients, and an increased efficacy with a more rapid onset of action.

SUMMARY OF THE INVENTION

The invention provides an effective topical treatment of rosacea, with a rapid onset of action.

Applicant surprisingly demonstrated that a composition comprising at least one compound of the avermectin family, and at least one non-steroidal anti-inflammatory compound (NSAID) allows a more effective treatment of rosacea, with fewer side effects irrespective of the duration of the application of this composition. In particular, such composition makes it possible to obtain a more rapid and greater reduction in the symptoms of rosacea with a time sustainable effect and few side effects. More precisely, such composition allows to effectively treat and/or prevent the inflammatory lesions of type II rosacea such as papules and pustules with a very rapid onset of action.

The present invention therefore concerns a composition comprising a pharmaceutically acceptable carrier, at least one compound of the avermectin family, and at least one non-steroidal anti-inflammatory compound.

In a preferred embodiment, the compound of the avermectin family is chosen from the group consisting of ivermectin, invermectin, avermectin, abamectin, doramectin, eprinomectin and selamectin, aversectin B, AB or C, emamectin B1 a, emamectin B1 b, latidectin and their derivatives. Preferably, the compound of the avermectin family is ivermectin.

In a further preferred embodiment, the non-steroidal anti-inflammatory compound is chosen from the group consisting of salicylates, propionic acid derivatives, acetic acid derivatives, enolic acid derivatives, fenamic acid derivatives, selective COX-2 inhibitors, and sulphonanilides. In a more preferred embodiment, the non-steroidal anti-inflammatory compound is acetic acid derivatives such as diclofenac, indomethacin, sulindac, elodac, ketorolac, and nabumetone. Preferably, the non-steroidal anti-inflammatory compound is diclofenac and its salts.

In a particular embodiment, the compound of the avermectin family is present at a concentration from 0.001 to 10%, preferably from 0.01 to 5%, and more preferably 1% by weight relative to the total weight of the composition.

In a further particular embodiment, the non-steroidal anti-inflammatory compound is present at a concentration from 0.001 to 10%, preferably from 0.001 to 5%, more preferably from 0.1 to 3% and in particular 1% or 3% by weight relative to the total weight of the composition.

Preferably, the composition of the invention is for a topical application.

In a preferred embodiment, the composition is in the form of salves, emulsions, creams, milks, ointments, impregnated pads, syndets, solutions, gels, sprays or aerosols, foams, suspensions, lotions or sticks. In a more preferred embodiment, the composition is in the form of emulsion.

Another object of the invention is a composition as disclosed herein comprising at least one compound of the avermectin family and at least one non-steroidal anti-inflammatory compound, for use in the treatment and/or prevention of rosacea.

The present invention further relates to the use of a composition as disclosed herein for the manufacture of a medicament for treating and/or preventing rosacea.

The present invention also relates to a method for treating and/or preventing rosacea comprising administering a composition as disclosed herein in a subject suffering of rosacea.

In a preferred embodiment, rosacea is selected in the group consisting of type I erythematous rosacea, type II papulopustular rosacea and ocular rosacea. In a more preferred embodiment rosacea is type II papulopustular rosacea.

DETAILED DESCRIPTION OF THE INVENTION

The applicant found that a composition comprising at least one avermectin family compound, and at least one non-steroidal anti-inflammatory compound is effective for treating and/or preventing rosacea, such as type I, type II and ocular rosacea, preferably by topical application. Even more specifically, the applicant demonstrated that a composition comprising ivermectin and diclofenac is effective for topically treating and/or preventing rosacea, especially type I, type II and ocular rosacea, and preferably type II rosacea. Even more specifically, the applicant surprisingly found that a composition comprising ivermectin and diclofenac allows to effectively treat and/or prevent the inflammatory lesions of type II papulopustular rosacea with a rapid onset of action.

Indeed as demonstrated in the experimental section of the present invention, the topical application of a composition comprising 1% of ivermectin, and 1% of diclofenac allows to significantly decrease the arachidonic acid-induced ear edema in the BALB/c mice model. This anti-inflammatory effect is significantly greater than the effect observed with ivermectin and diclofenac alone. Moreover a sustained anti-inflammatory effect is observed until 4 hours after the topical application.

Knowing that rosacea is characterized by transitory and/or persistent central facial erythema and transient inflammatory lesions such as papules and/or pustules in the center of the face, the composition as disclosed herein for topical application is useful for treating and/or preventing rosacea.

More specifically, this improved effect demonstrated with the topical application of a composition comprising ivermectin and diclofenac is useful for treating and/or preventing type II papulopustular rosacea by decreasing the number of inflammatory lesions such as papules and pustules.

The present invention concerns a composition comprising a pharmaceutically acceptable carrier, at least one compound of the avermectin family, and at least one non-steroidal anti-inflammatory compound.

According to one embodiment, the compound of the avermectin family is advantageously chosen from ivermectin, invermectin, avermectin, abamectin, doramectin, eprinomectin and selamectin, aversectin B, AB or C, emamectin B1 a, emamectin B1 b, latidectin and their derivatives. Avermectin derivatives according to the present invention refers to compounds produced by avermectin derivatization, generally obtained by exploiting the reactive centers of molecules, since these groups in turn are totally responsible for stability profile as well as anthelmintic activities of avermectin compounds.

In a more preferred embodiment, the compound of the avermectin family is ivermectin and its optical isomers.

According to one embodiment, the non-steroidal anti-inflammatory compound is chosen from the group consisting of salicylates, propionic acid derivatives, acetic acid derivatives, enolic acid derivatives, fenamic acid derivatives, selective COX-2 inhibitors and sulphonanilides. In a preferred embodiment, the non-steroidal anti-inflammatory compound is preferably chosen from the group of acetic acid derivatives and is preferably diclofenac and its salts.

In a preferred embodiment, the avermectin family compound is ivermectin and the non-steroidal anti-inflammatory compound is diclofenac.

In a more preferred embodiment, the composition as disclosed herein comprises at least one compound of the avermectine family, preferably ivermectine and at least one anti-inflammatory compound, preferably diclofenac and its salts, as sole active ingredients. According to this embodiment, the composition comprises no further active ingredient.

The present invention is also directed to a composition comprising a pharmaceutically acceptable carrier, at least one compound of the avermectin family, and at least one non-steroidal anti-inflammatory compound for use for the treatment and/or the prevention of rosacea.

Particularly, the composition of the invention comprises from 0.001 to 10% by weight of a compound of the avermectin family relative to the total weight of the composition, more preferably from 0.01 to 5%, and in particular 0.75%, 1%, 1.5% or 2%. Preferably the composition comprises 1% by weight of a compound of the avermectin family relative to the total weight of the composition. Particularly, the composition of the invention comprises from 0.001 to 10%, by weight of the non-steroidal anti-inflammatory compound relative to the total weight of the composition, from 0.001 to 5%, preferably from 0.1 to 3% and more preferably 1% or 3% by weight of the non-steroidal anti-inflammatory compound relative to the total weight of the composition.

The choice of the concentration of the avermectin family compound and the non-steroidal anti-inflammatory compound for the treatment of rosacea can be made depending on the type and severity of the disease, and location of the affected area. A person of ordinary skill in the art will be able to determine these different parameters.

The present invention is also directed to a method for treating and/or preventing rosacea comprising the topical administration of a composition comprising at least one compound of the avermectin family, and at least one non-steroidal anti-inflammatory compound (NSAID) in a subject in need thereof.

Preferably, the compound of the avermectin family is chosen from the group consisting of ivermectin, avermectin, abamectin, doramectin, eprinomectin and selamectin, aversectin B, AB or C, emamectin B1a, emamectin B1b, latidectin and their derivatives. More preferably, the compound of the avermectin family is ivermectin.

Ivermectin is a mixture of two compounds belonging to the avermectin class, 5-O-demethyl-22,23-dihydroavermectin A1a and 5-O-demethyl-22,23-dihydroavermectin A1b. They are also known as 22,23-dihydroavermectin B1a and 22,23-dihydroavermectin B1b. Ivermectin contains at least 80% of 22,23-dihydroavermectin B1a and less than 20% of 22,23-dihydroavermectin B1b. This active agent is part of the avermectin class, a group of macrocyclic lactones produced by the bacterium *Streptomyces avermitilis*.

In the middle of the 1980s, ivermectin was presented as a broad-spectrum antiparasitic medicinal product for veterinary use (Campbell et al.: Science, 1983, 221, 823-828). Ivermectin is effective against most common intestinal worms, except tapeworms, most acarids and some lice. In particular, it exhibits considerable affinity for the glutamate dependent chloride channels present in invertebrate nerve cells and muscle cells. Its binding to these channels promotes an increase in membrane permeability to chloride ions, resulting in hyperpolarization of the nerve or muscle cell. Neuromuscular paralysis which can lead to the death of certain parasites results therefrom. Ivermectin also interacts with other ligand dependant chloride channels, such as those involving the neuromediator GABA (gammaaminobutyric acid).

Ivermectin is more particularly disclosed as an anthelmintic used in humans for the treatment of river blindness caused by *Onchocerca volvulus*, of gastrointestinal strongyloidiasis (anguillulosis) (product Stromectol®), and of human scabies (Meinking et al., N. Engl. J. Med., 1995, 333, 26-30). Manetta and Watkins (WO 2004/093886) have suggested the use of ivermectin for producing a topical pharmaceutical composition for the treatment of rosacea and other dermatological disorders.

Particularly, the composition of the invention comprises from 0.001 to 10% by weight of a compound of the avermectin family relative to the total weight of the composition, more preferably from 0.01 to 5%, and in particular 0.75%, 1%, 1.5% or 2%. Preferably the composition comprises 1% by weight of a compound of the avermectin family relative to the total weight of the composition.

According to a specific embodiment, the compositions comprising avermectin family compound useful for the invention are the emulsions described in the U.S. Pat. No. 7,550,440 B2. More specifically the useful avermectin compositions are emulsions comprising: an oily phase comprising dimethicone, cyclomethicone, isopropyl palmitate and/or isopropyl myristate, said oily phase further comprising fatty substances selected from the group consisting of cetyl alcohol, cetostearyl alcohol, stearyl alcohol, palmitostearic acid, stearic acid and self-emulsifiable wax; at least one surfactant-emulsifier selected from the group consisting of glyceryl/PEG100 stearate, sorbitan monostearate, sorbitan palmitate, Steareth-20, Steareth-2, Steareth-21 and Ceteareth-20; avermectin compound and especially ivermectin; a mixture of solvents and/or propenetrating agents selected from the group consisting of propylene glycol, oleyl alcohol, phenoxyethanol and glyceryl triacetate; acrylate C10-C30 alkyl acrylate crosspolymer gelling agent, and water.

In a specific embodiment the preferred avermectin composition comprises 1% of ivermectine and more specifically it is Soolantra®.

According to the present invention "non-steroidal anti-inflammatory drugs (NSAID)" refers to a group of drugs with analgesic and antipyretic effects and which have, in higher doses, anti-inflammatory effects. They are usually indicated for the treatment of acute or chronic conditions where pain and inflammation are present. NSAIDs inhibit the activity of both cyclooxygenase-1 (COX-1) and cyclooxygenase-2 (COX-2), and thereby, the synthesis of prostaglandins and thromboxanes. It is thought that inhibiting COX-2 leads to the anti-inflammatory, analgesic and antipyretic effects. Preferably, the non-steroidal anti-inflammatory compound may be selected among the group of compounds consisting of salicylates, propionic acid derivatives, acetic acid derivatives, enolic acid derivatives, fenamic acid derivatives, selective COX-2 inhibitors and sulphonanilides.

For instance the salicylates may be selected from the group consisting of aspirin, diflunisal and salsalate. The propionic acid derivative may be selected from the group consisting of ibuprofen, naproxen, fenoprofen, flurbiprofen, loxoprofen, and oxaprozin. The acetic acid derivative may be selected from the group consisting of diclofenac, indomethacin, sulindac, elodolac, ketorolac, and nabumetone. The enolic acid (oxicam) derivative may be selected from the group consisting of piroxicam, tenoxicam, droxicam, lornoxicam, and isoxicam. The fenamic acid derivative (fenamates) may be selected from the group consisting of mefenamic acid, meclofenamic acid, flufenamic acid, and tolfenamic acid. The selective COX-2 inhibitor (Coxibs) may be selected from the group consisting of celecoxib, rofecoxib, valdecoxib, parecoxib, lumiracoxib, etoricoxib, and firocoxib. The sulphonanilide may be nimesulide.

In a preferred embodiment, the non-steroidal anti-inflammatory compounds are chosen among the group of acetic acid derivatives. More preferably, the preferred non-steroidal anti-inflammatory compound is diclofenac and its salts.

Diclofenac, also called 2-(2-(2,6-dichlorophenylamino) phenyl)acetic acid, is available in several different topical formulations, such as 1% diclofenac sodium gel (Voltaren® Gel, diclofenac diethylamine gel 1.16% (Voltarol, Emulgel®), 3% diclofenac sodium gel (Solaraze®), diclofenac spray 4% gel (MIKA Pharma GmbH), 2% diclofenac DMSO lotion (PENNSAID®), and diclofenac epolamine (diclofenac hydroxyethyl-pyrrolidine) patch (Flector® Patch). All of the abovementioned topical compositions are suitable for the present invention.

A preferred pharmaceutical composition comprising at least one non-steroidal anti-inflammatory compound in a pharmaceutically acceptable carrier is Solaraze® composition, which is a 3% diclofenac sodium gel.

In a preferred embodiment, the composition of the invention comprises from 0.001 to 10%, by weight of the non-steroidal anti-inflammatory compound relative to the total weight of the composition, preferably from 0.001 to 5%, more preferably from 0.1 to 3% and even more preferably 1% or 3% by weight of the non-steroidal anti-inflammatory compound relative to the total weight of the composition.

The compositions as disclosed herein are in particular intended for topical application to the skin and/or for ocular application to the eyes.

According to the invention, the composition is formulated in a pharmaceutically acceptable carrier. The carrier must be "acceptable" in the sense of being compatible with the other ingredients of the formulations and not deleterious to the recipient thereof. Particularly, in the context of the invention, the carrier is compatible with human skin.

The composition is advantageously administered by topical application and, therefore, is in a form suitable for topical application to the skin. For example, it may be in the form of an optionally gelled, oily solution, an optionally two-phase dispersion of the lotion type, an emulsion obtained by dispersion of a fatty phase in an aqueous phase (O/W) or vice versa (W/O), or a triple emulsion (W/O/W or O/W/O) or a vesicular dispersion of ionic and/or non-ionic type. This topical composition may be in an anhydrous form, in an aqueous form or in to form of an emulsion. These compositions are prepared according to the usual methods. Preferably, a composition in the form of an emulsion obtained by dispersion of a fatty phase in an aqueous phase (O/W) is used.

Preferably, the composition as defined in the present application is a dermatological composition.

This composition may be more or less fluid and may be in the form of salves, emulsions, creams, milks, ointments, impregnated pads, syndets, solutions, gels, sprays or aerosols, foams, suspensions, lotions or sticks. Preferably, the composition used in the present invention is in the form of an emulsion, of a cream, of a lotion type, of a gel, or of a solution, and more preferably in the form of an emulsion.

It is also considered that the composition according to the present invention may further comprise an additional active ingredient or additive. The additional active ingredient is preferably chosen among antibiotics, antibacterials, antivirals, antiparasitics, antifungals, anesthetics, analgesics, antiallergic agents, retinoids, free-radical scavengers, anti-pruriginous, keratolytic agents, antiseborrheics, antihistaminics, sulfides, immunosuppressant products and antiproliferative agents, corticosteroids, intravenous immunoglobulin, anti-angiogenic, anti-inflammatory and/or a mixture thereof. The additive is preferably selected from the group consisting of sequestering agents, chelating agents, antioxidants, sunscreens, preservatives, fillers, electrolytes, humectants, dyes, conventional acids, or bases, organic or inorganic, perfumes, essential oils, cosmetic active agents, moisturizers, vitamins, essential fatty acids, sphingolipids, self-tanning compounds, soothing and protective agents of the skin, penetrating agents, emulsifiers, gelling agents and a mixture thereof.

As used herein, the term "treatment" or "treating" refers to an improvement, the prophylaxis of a disease or disorder, preferably rosacea, in the context of the present invention, or at least one symptom can be discerned therefrom. "Treatment" or "treating" also means an improvement, prevention of at least one measurable physical parameter associated with the disease or disorder, preferably rosacea, which is not necessarily discernible in the subject. "Treatment" or "treating" further refers to inhibiting or slowing the progression of a disease or disorder, preferably rosacea, physically, e.g., stabilization of a discernible symptom, physiologically, for example, stabilization of a physical parameter, or both. "Treatment" or "treating" further refers to delaying the onset of a disease or disorder, preferably rosacea. In some embodiments, the composition comprising the compounds of interest is administered as a preventive measure. In this context, "prevention" or "preventing" refers to a reduction in the risk of acquiring a disease or disorder specified, preferably rosacea.

In the context of the present invention, the term "pharmaceutical composition" refers preferably to a dermatological composition, which can be topically applied. "Topical application" refers to the skin, the mucous membranes and/or the ocular area.

The present invention is directed to any mammal, particularly humans, male or female.

In a preferred embodiment, rosacea is chosen among the group comprising type I erythematous rosacea, type II papulopustular rosacea, ocular rosacea, preferably type II papulopustular rosacea In one embodiment, the present invention refers to a method of treatment and/or prevention of rosacea, comprising the administration of a composition as disclosed herein in a therapeutically effective amount in a subject in need thereof. In a particular embodiment, the composition is administered in a single administration or alternatively comprises several applications. In a particular embodiment, the composition may be administered at least once a week. In a further particular embodiment, the composition may be administered about one time per week to about once or twice daily for a given treatment.

In a preferred embodiment, the composition of the present invention is administered once a day.

The person skilled in the art will be able to define the treatment and/or prevention parameters such as the administration frequency, the dosage for each active ingredient and the composition form.

Following examples illustrate further aspects and advantages of the invention which are no way limiting in nature.

EXAMPLES

Example 1: Evaluation of the Anti-Inflammatory Activity of Ivermectin and Diclofenac after a Single Topical Application in the Arachidonic Acid-Induced Mouse Ear Edema Test on Balb/c Mice 1) Material and Methods
Arachidonic acid is dissolved in a mixture of THF/Methanol at 4%.
Tested compounds were dissolved in arachidonic acid solution, at final concentration.
20 µl of the tested compound is dissolved in arachidonic acid solution and applied on the internal side of the right ear.
The ear thickness is measured at T=0 h, T+1 h, T+2 h, T+4 h.
THF/Methanol is used as vehicle control.
Indomethacin 5% is used as positive control and arachidonic acid at 4% in THF/Methanol is used as inductor of inflammation.
2) Results
Ear thickness measurement after 1 h demonstrated that the positive control with indomethacin at 5% inhibits the ear edema caused by arachidonic acid by 95%. Ivermectin 1% alone, reduces the ear edema by 56%. Diclofenac 1% alone reduces the ear edema 68%. The combination of ivermectin 1% with diclofenac 1% inhibits the ear edema caused by arachidonic acid by 96.8%.
Ear thickness measurement after 2 h demonstrated that the positive control with indomethacin at 5% inhibits the ear edema caused by arachidonic acid by 94%. Ivermectin 1% alone, reduces the ear edema by 47%. Diclofenac 1% alone reduces the ear edema 75%. The combination of ivermectin 1% with diclofenac 1% inhibits the ear edema caused by arachidonic acid by 100%.
Ear thickness measurement after 4 h demonstrated that the positive control with indomethacin at 5% inhibits the ear edema caused by arachidonic acid by 92.5%. Ivermectin 1% alone, reduces the ear edema by 54%. Diclofenac 1% alone reduces the ear edema 78%. The combination of ivermectin 1% with diclofenac 1% inhibits the ear edema caused by arachidonic acid by 98.5%.
These results clearly demonstrated that a composition comprising ivermectin 1% and diclofenac 1% topically applied is able to induce a significantly greater inhibition of the ear edema in comparison to ivermectin 1% alone and to diclofenac 1% alone. This significant inhibition of the ear edema induced by the composition comprising ivermectin 1% and diclofenac 1% is sustained at least until 4 h after topical treatment. These results demonstrate a significant high efficacy of anti-inflammatory effect of the composition comprising the combination of ivermectin 1% and diclofenac 1% on arachidonic acid-induced ear edema.

TABLE 1

Represents the average measurement of the thickness of the ear edema. The average measurement of the thickness of the ear obtained with the non-treated group (control group) is compared to the average measurement of the thickness of the ear obtained after treatment with: 4% arachidonic acid, 1% ivermectin, 1% diclofenac and the combination of 1% ivermectin and 1% diclofenac.

| Compounds/Doses | 1 h measurement | | 2 h measurement | | 4 h measurement | |
|---|---|---|---|---|---|---|
| | Mean ear edema | Inhibition vs AA 4% | Mean ear edema | Inhibition vs AA 4% | Mean ear edema | Inhibition vs AA 4% |
| Arachidonic acid (AA) 4% | 18.8 | *** | 16.2 | *** | 13.4 | *** |
| AA+ indomethacin 5% | 1 | 94.7 | 1 | 93.8 | 1 | 92.5 |
| AA+ ivermectin 1% | 8.2 | 56.4 | 8.6 | 46.9 | 6.2 | 53.7 |
| AA+ diclofenac 1% | 6 | 68.1 | 4 | 75.3 | 3 | 77.6 |
| AA+ ivermectin 1% + diclofenac 1% | 0.6 | 96.8 | −0 | 100 | 0.2 | 98.5 |

The invention claimed is:

1. A composition comprising:
   (a) ivermectin, present at a concentration of 0.01 to 5% by weight, relative to the total weight of the composition;
   (b) diclofenac or a pharmaceutically acceptable salt thereof, present at a concentration of 1% to 3% by weight, relative to the total weight of the composition; and
   (c) a pharmaceutically acceptable carrier,
   wherein the composition is formulated for topical application.

2. The composition according to claim 1, wherein the composition is in the form of a salve, an emulsion, a cream, a milk, an ointment, an impregnated pad, a syndet, a solution, a gel, a spray an aerosol, a foam, a suspension, a lotion or a stick.

3. The composition according to claim 2, wherein the composition is in the form of an emulsion.

4. A method of treating or preventing rosacea in a subject in need thereof, the method comprising topically administering the composition of claim 1 to the subject.

5. The method according to claim 4, wherein rosacea is selected in the group consisting of type I erythematous rosacea, type II papulopustular rosacea and ocular rosacea.

6. The method according to claim 5, wherein rosacea is type II papulopustular rosacea.

7. The composition according to claim 1, wherein the ivermectin is present at a concentration of 0.75%, 1%, 1.5%, or 2% by weight relative to the total weight of the composition.

8. The composition of claim 1, wherein the ivermectin is present at a concentration of 1% relative to the total weight of the composition.

9. The composition of claim 1, wherein the ivermectin and the diclofenac or pharmaceutically acceptable salt thereof are the sole active ingredients in the composition.

* * * * *